United States Patent [19]

DiLeo et al.

[11] Patent Number: 5,282,380
[45] Date of Patent: Feb. 1, 1994

[54] INTEGRITY TEST FOR MEMBRANES

[75] Inventors: Anthony J. DiLeo, Westford; Michael W. Phillips, Burlington, both of Mass.

[73] Assignee: Millipore Corporation, Bedford, Mass.

[21] Appl. No.: 906,730

[22] Filed: Jun. 30, 1992

[51] Int. Cl.$^5$ ............................................. G01N 15/08
[52] U.S. Cl. ........................................................ 73/38
[58] Field of Search ............................................. 73/38

[56] References Cited

U.S. PATENT DOCUMENTS

| | | | |
|---|---|---|---|
| 4,701,861 | 10/1987 | Kauke | 73/38 X |
| 4,872,974 | 10/1989 | Hirayama et al. | 73/38 X |
| 4,881,176 | 11/1989 | Kononov | 73/38 X |
| 5,064,529 | 11/1991 | Hirayama et al. | 73/38 X |

FOREIGN PATENT DOCUMENTS

| | | | |
|---|---|---|---|
| 3312729 | 10/1984 | Fed. Rep. of Germany | 73/38 |
| 142445 | 5/1992 | Japan | 73/38 |
| 1679295 | 9/1991 | U.S.S.R. | 73/38 |

*Primary Examiner*—Hezron E. Williams
*Assistant Examiner*—Joseph W. Roskos
*Attorney, Agent, or Firm*—Andrew T. Karnakis; Paul J. Cook

[57] ABSTRACT

A process is provided for rapidly and non-destructively evaluating the particle retention characteristics of porous membranes using a novel liquid-porosimetric technique. A ratio of two membrane permeabilities is measured at preselected operating conditions using a pair of mutually immiscible fluids, one of which is employed as a membrane wetting agent and the other used as an intrusion fluid. The first operating condition, a particular transmembrane pressure, is chosen so as to selectively intrude those pores accessible to a given sized particle, such as a virus. The second operating condition, either a second preselected transmembrane pressure or a water permeability measurement, is chosen such that nearly all of the membrane pores are intruded. The ratio of the two permeabilities obtained with each set of operating conditions is thus the percentage of total flow through the membrane pores accessible to a given sized particle. By experimentally measuring this permeability ratio on membranes with known particle retention behavior, a calibration curve relating the permeability ratio to the particle retention characteristics can be constructed. From this standard correlation, the particle retention capabilities of an unchallenged membrane can be predicted in a non-destructive manner solely by measuring its permeability ratio.

14 Claims, 4 Drawing Sheets

INTEGRITY TEST FOR MEMBRANES

BACKGROUND OF THE INVENTION

This invention relates to a process for non-destructively evaluating the integrity of porous membranes such as ultrafiltration membranes. More particularly, this invention relates to a non-destructive testing process for quantitatively determining the effect of undesirable large pores in a membrane which, when present, drastically degrade the membrane's particle retention capabilities.

It is widely believed that the majority of pores present in ultrafiltration (UF) membranes ($\approx 80\%$) lie within a narrow range of the pore distribution. However, since the membrane permeability, and consequently, the transmembrane transport depend upon the fourth power of the pore radius, these smaller pores usually contribute less than 10% to the total membrane permeability. As a consequence, a very small number of large-sized pores actually control the membrane performance. For membranes whose particle retention is based upon a sieving mechanism, the evaluation of the "active" pore size distribution is of cardinal importance in predicting the selective transport through such membranes. Therefore, to accurately correlate particle retention, it is necessary to characterize these larger "transport controlling" pores.

The bubble point test and the air diffusion tests are two non-destructive integrity tests which have been previously employed in an attempt to correlate and predict particle retention for various classes of membranes. In the bubble point test, a thoroughly wetted membrane is placed into a housing and contacted with air. The upstream air pressure is then gradually increased, eventually resulting in the selective intrusion of air through the largest pores and the subsequent formation of air bubbles downstream of the membrane. Assuming cylindrical pores, the pore radius corresponding to the pressure at which these bubbles are first observed (bubble point) can be approximated by the modified Young-Laplace capillary equation given by $$P = \frac{4 K \gamma \cos\theta}{d_p} \quad (1)$$

where P is the transpore pressure drop, $d_p$ is the pore diameter intruded, $\theta$ is the contact angle, K represents a shape correction factor, and $\gamma$ is the air-liquid interfacial tension. Since capillary forces dictate that the largest pores are those first intruded with air, the bubble point test can be considered a measure of the largest pore present in the given membrane sample. It is the characterization and quantification of these largest pores which is essential for developing a test capable of correlating and predicting particle retention. However, two problems exist with the traditional bubble point test as it pertains to the evaluation of ultrafiltration membranes. First, due to the extremely large interfacial surface tension at the air/liquid interface, the pressures required to observe the bubble point for typical ultrafiltration (UF) membranes are in excess of 500 psi. Conventional UF membranes usually compress when subjected to pressures in this range, leading to erroneous results. Second, as the membrane area to be tested increases, the actual membrane bubble point becomes more difficult to detect due to the large background of air diffusing through the wetted membrane. Although this problem can be minimized by utilizing a gas that has a low solubility in the wetting liquid, diffusion due to solubility effects can not be totally eliminated. Consequently, this test is essentially limited to small area microfilters.

In the air diffusion test, the membrane is again wetted and contacted with air. The air pressure is increased to some prescribed value below the membrane's bubble point and the total amount of air flow through the wetted membrane by diffusion and convection is recorded. Since the operating pressure is usually well below the bubble point of the membrane, integral membranes exhibit only diffusional flow. In fact, only gross defects present in the membrane sample, those which contribute measurable convective air flow, can be detected. Thus, on a theoretical basis, this test can not be expected to correlate well to particle retention of integral membranes since this test has sensitivity only to gross defects.

A permoporometric technique for the characterization and pore size distribution determination of various classes of UF membranes is disclosed by:

"Membrane Morphology and Transport Properties", *Desalination*, 53 11 (1985),

"Computer Driven Porosimeter for Ultrafiltration Membranes", *Characterisation of Porous Solids*, K. K. Unger, et al., eds., 283 (1988), "Permoporometric Study on Ultrafiltration Membranes", *J. Membrane Sci.*, 41 69 (1989), and "Correlation of Direct Porosimetric Data and Performance of Ultrafiltration Membranes", *Proc. Biochem. Int'l.*, 111 (1990). In this permoporometric technique, the air-liquid interface typically encountered in bubble point testing is now replaced with the interface between two immiscible liquids. The key advantage with utilizing a two phase liquid system is the extremely small interfacial tensions associated with many pairs of immiscible liquids, resulting in low transmembrane pressures necessary to selectively intrude nanometer sized pores. In addition, since the two phases are completely immiscible, there is no background diffusional flow to contend with, resulting in a technique which is linearly scalable and independent of membrane surface area. Thus, this technique is eminently suitable for the characterization of UF membranes.

In the disclosed permoporometric technique, a membrane sample is first wetted with one of two mutually immiscible liquid phases (wetting phase). The other immiscible liquid phase (intrusion phase) is then placed upstream of the membrane housing. The intrusion phase is then sequentially pumped through the membrane sample at prescribed flow rates and the resulting equilibrium upstream pressures recorded. As with the bubble point test, the first pores intruded at the lowest flow rates (lowest pressures) are the largest pores present in the membrane sample. However, the use of two immiscible fluids with an extremely low interfacial surface tension has the advantage of requiring pressures less than 20 psi for the complete intrusion of these larger pores present in UF membranes. With knowledge of the upstream pressures corresponding to the various intrusion phase flow rates, the interfacial surface tension of the two immiscible fluids, and assuming the validity of a particular mathematical model, this test is able to calculate an effective pore size distribution of the membrane sample. Based on this entire calculated pore size distribution, the performance of conventional UF membranes were able to be correlated.

There are two major limitations associated with the disclosed technology as it pertains to rapidly and non-destructively correlating the particle retention capabilities of ultrafiltration membranes. First, the disclosed technology relies upon the generation of an entire effective pore size distribution for the tested membrane samples, an extremely tedious process which may take upwards of 2-3 hours or longer depending on the desired degree of accuracy. In addition, the two phase system disclosed by these references throughout the UF characterization experiments is an isobutanol: methanol:water (15:7:25 v/v/v) system. This solvent system may be difficult to remove from conventional UF membranes and is toxic to most biological fluids. For these reasons, any test involving the use of this particular two phase system may render the test destructive.

It would be desirable to provide a rapid integrity test for ultrafiltration membranes which is both non-destructive and circumvents the tedious process of determining an entire effective pore size distribution for each membrane sample tested. Furthermore, it would be desirable to provide such a test which is independent of membrane surface area, porosity, and thickness; variables which can differ widely between membrane samples and often compound the difficulty in interpreting many integrity test results. Additionally, it would be desirable to provide such a test which permits predicting with a high degree of accuracy whether a particular UF membrane is capable of retaining particles of a given size, such as viruses, while avoiding the need to actually challenge said membrane with a liquid solution containing the particles in order to make the determination.

SUMMARY OF THE INVENTION

The present invention is based on the discovery that, with novel modifications to the disclosed permoporometric technology, a rapid and scalable non-destructive test can be developed for ultrafiltration membranes that reproducibly correlates and predicts the retention of various sized particles, such as viruses. Unlike the prior art, which relied on both the validity of a mathematical model and the measurement of numerous transmembrane pressures corresponding to stepwise increases in the intrusion phase flow rate to calculate an effective pore size distrubtion, the present invention relies upon the generation of only two data points to calculate a characteristic flow rate ratio. Using liquid-liquid intrusion technology, a ratio of two membrane permeabilities is measured at preselected operating conditions using a pair of mutually immiscible fluids, one of which is employed as a membrane wetting agent and the other used as an intrusion fluid. The first operating condition, a particular transmembrane pressure, is chosen so as to selectively intrude pores within a given size range. For a specific two phase system, this first operating pressure is dependent solely upon the size of particle one is trying to correlate the retention of. The second operating condition, either a second preselected transmembrane pressure or a water permeability measurement, is chosen such that nearly all of the membrane pores are intruded. The logarithm of the ratio of these two permeability measurements, along with an appropriate standard curve, is a direct non-destructive measure of the particle retention capabilities of the tested membrane sample.

Since a ratio of two permeability measurements is taken, the resulting value is independent of membrane surface area, porosity, tortuosity, and thickness. This is advantageous since a given ultrafiltration membrane can be configured in modules of varying size and the requirement for multiple integrity tests is eliminated. In addition, by selecting an appropriate two phase system whose constituents are both easily flushed from the membrane structure and do not adversely interact with said membrane, the developed correlative test can be rendered non-destructive. This is also advantageous since the test can then be used both pre- and post-use to validate the ultrafiltration membrane integrity.

The standard curve required to predict the particle retention capabilities of unchallenged membranes is developed in the following manner. First, a sample of the ultrafiltration membrane is challenged with a liquid solution containing non-absorbing particles of known size, such as virus particles, to determine the particle retention capabilites of the membrane. The $\log_{10}$ of the ratio of retentate particle concentration to permeate particle concentration is termed the LRV and is a measure of the inherent particle retention capabilities of the membrane sample. The membrane sample is then characterized by the developed liquid-liquid intrusion test by taking a permeability ratio of flow rates as discussed above. Repeating this exercise with ultrafiltration membrane samples of varying LRV values, a standard curve relating the particle retention capabilities to the measured flow rate ratio can be constructed. From this developed standard correlation, the particle retention capabilities of an unchallenged membrane can be predicted in a non-destructive manner solely by measuring its permeability ratio.

DESCRIPTION OF SPECIFIC EMBODIMENTS

Figure 1:
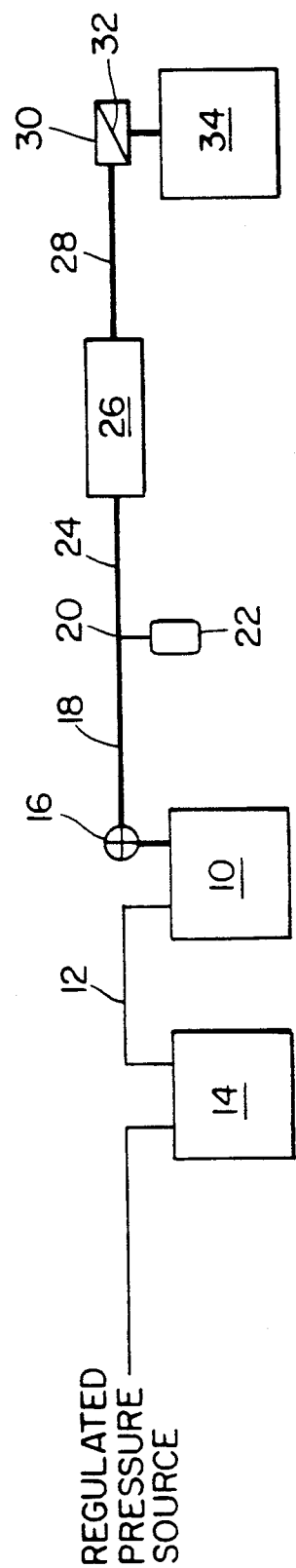
FIG. 1 is a schematic view of the apparatus utilized in Examples 1 and 2 for measuring the membrane integrity test values.

The performance of any ultrafiltration membrane is based on its ability to retain specific solutes or suspended solids. The existence of undesirably large pores within ultrafiltration membranes can drastically degrade its ability to efficiently retain particles, such as viruses. In addition, to completely validate the membrane process step, it is necessary to have some means of verifying pre- and post-use membrane integrity. For these reasons, it is imperative that an appropriate non-destructive test be developed which actually characterizes and quantifies the existence of these larger pores present in ultrafiltration membranes. Consequently, a novel scalable liquid-liquid intrusion integrity test has been developed which rapidly and non-destructively correlates and predicts the particle retention capabilities of ultrafiltration membranes. Examples of such membranes include composite membranes which function as ultrafiltration membranes, such as those disclosed in U.S. Pat. No. 5,017,292 which is incorporated herein by reference, conventional asymmetric UF membranes, or the like.

The present invention is based upon the use of novel modifications to the disclosed liquid permoporometric technique wherein a constant transmembrane pressure or constant transmembrane flow rate is carefully controlled. Either (a) a ratio of two membrane permeabilities measured at preselected constant transmembrane operating pressures or (b) a ratio of two transmembrane flow rates selected so as to achieve preselected transmembrane pressures is determined for a given ultrafiltration membrane using a pair of mutually immiscible fluids, one of which is employed as a membrane wetting agent and the other used as an intrusion fluid. One or both of these ratios is then compared to a previously determined standard curve developed for the same class of membrane which correlates a particle retention characteristic, such as the log retention value (LRV; the negative logarithm of the sieving coefficient) to either measured ratio determined from step (a) or (b).

The standard curve is obtained by both challenging samples of similar ultrafiltration membranes with a liquid containing particles of a known size, such as virus particles, and measuring the characteristic flow ratio determined in accordance with the present invention. Once the standard curve has been developed, the ability of an ultrafiltration membrane for retaining particles, such as virus particles, can be determined by measuring its characteristic ratio obtained from either the constant transmembrane pressure or constant transmembrane flow rate procedure. The standard curve permits a direct measure of the particle retention capabilities of the tested membrane sample to be made without the need to actually challenge the ultrafiltration membrane with particles of a specific size, such as virus particles.

The motivation for determining a characteristic ratio is twofold. First, from a theoretical standpoint, an appropriately determined ratio can be shown to be an approximate measure of the membrane LRV. Assuming rigid, spherical particles of diameter $d_p$, and neglecting hydrodynamic forces which normally oppose the unhindered transport of solutes through membrane pores, the membrane LRV can be approximated as $$LRV \approx \log \frac{Q_{tot}}{Q_{dp}} \qquad (2)$$

where $Q_{tot}$ is the total amount of flow through the membrane sample under a given set of operating conditions and $Q_{dp}$ represents the amount of flow through those membrane pores equal in size or larger than $d_p$, the solute particle diameter. The developed liquid-liquid intrusion technology is eminently suitable for measuring this flow rate ratio. Second, this novel approach of taking the ratio of two different permeabilities allows the integrity test value to be unaffected by differences in membrane surface area, porosity, tortuosity, and thickness. Thus, one value (the ratio) essentially characterizes an ultrafiltration membrane with regards to its ability to retain a particular sized particle, allowing the non-destructive comparison of different membranes. In addition, a given ultrafiltration membrane can be configured within modules of varying size and the requirement for multiple integrity tests is eliminated.

In order to measure the constant transmembrane pressure characteristic ratio, the membrane sample is first wet with one of two immiscible fluids (wetting phase). The other immiscible fluid (intrusion phase) is placed upstream of the membrane sample and pressurized to some prescribed level chosen to selectively intrude those pores accessible to a particular sized particle. This specific operating pressure is dependent upon both the size of particle one is trying to correlate the retention of and the particular two phase liquid system employed for the testing. After the system has been allowed to equilibrate, the resulting equilibrium intrusion phase flow rate is measured. The second operating condition is chosen such that nearly all of the membrane pores are intruded. This can be accomplished by either (a) increasing the intrusion phase pressure to another prescribed level which effectively intrudes all of the membrane pores and again measuring the subsequent equilibrium intrusion phase flow rate or (b) obtaining another measurement related to the total membrane permeability, such as the water permeability. In essence, the flow measurement made at this second operating condition is a measure of the total permeability of the entire membrane sample, $Q_{tot}$, whereas the flow of intrusion phase at the lower pressure is a measure of the permeability of the largest pores present in the membrane sample accessible to a particular sized particle, $Q_{dp}$. As calculated in equation (2), the logarithm of the ratio of these two flow rates obtained from both sets of operating conditions, along with an appropriate standard curve, is then a direct non-destructive measure of the particle retention capabilities of the tested membrane sample.

Alternatively, a similar two-step procedure can be followed wherein the transmembrane flow rates are maintained so as to achieve specific transmembrane pressures. The membrane sample is first wet with one of the immiscible fluids (wetting phase) and the other immiscible fluid (intrusion phase) is placed upstream of the membrane sample. The intrusion phase is then pumped through the membrane sample at some arbitrarily low flow rate chosen to achieve a transmembrane pressure less than some value preselected to intrude those pores accessible to a given sized particle. The intrusion flow rate is then sequentially increased until the desired transmembrane pressure is achieved and maintained. The intrusion flow rate which maintains this target transmembrane pressure is thus the desired value. To effect the complete intrusion of all the membrane pores present within the membrane sample, the intrusion phase flow rate is then increased until a second preselected transmembrane pressure is achieved and maintained. As before, this second operating condition can be replaced with some other test procedure which results in a value related to the total membrane permeability, such as the water permeability, without loss of generality. The flow rate obtained under the first set of operating conditions is a measure of the flow through those pores present in the membrane sample which are accessible to a particular sized particle, $Q_{dp}$. Likewise, the flow rate obtained under the second set of operating conditions is a measure of the total permeability of the entire membrane sample, $Q_{tot}$. The logarithm of the ratio of these two flow rates obtained from both sets of operating conditions, as calculated in equation (2), along with an appropriate standard curve, is then a direct measure of the particle retention capabilities of the tested membrane sample. This technique may have applicability when extremely small flow rates are involved since the technology for reproducibly delivering small liquid flows is more advanced than the technology for reproducibly measuring small liquid flows.

An important step in the present invention is the a priori determination of the target transmembrane pressure required to selectively intrude those pores in the desired size range. First, an appropriate liquid two phase system of known or measurable interfacial surface properties must be selected to characterize the ultrafiltration membranes. With knowledge of the liquid-liquid interfacial surface tension ($\gamma$) and the specific particle size about which a correlation is to be determined, an approximate pressure range required to selectively intrude those pores greater than the given particle size can be determined using the modified Young/Laplace capillary equation given by equation (1). Second, by experimentally measuring the standard curves relating the integrity test flow rate ratio to the particle retention capabilities of the membrane samples at intermediate pressures within this calculated pressure range, one can determine the optimal pressure that both minimizes the correlation error while maximizing the test sensitivity. This procedure is illustrated in Example 1.

The two immiscible liquids which are utilized in the test should not damage or degrade the membrane so as to render the test non-destructive. That is, the liquids should not adversely effect the mechanical strength of the membrane such as would be the case where a liquid exhibits a solvent effect on the membrane. In addition, the liquids should be easily removable from the membrane or, if not completely removable, should not exhibit a toxic effect on liquid compositions to be treated with the membrane. For example, when biological liquids such as serum are to be filtered through the membrane to remove undersirable particles such as virus particles, the liquid retained within the membrane pores, if any, should not degrade the proteins within the serum. An example of such an innocuous system is the two phase system formed upon mixing polyethylene glycol (MW 8000), ammonium sulfate, and water in a weight ratio 10:15:75. This two phase system possesses a low interfacial surface tension, a necessary property required of the two phase system in order to intrude nanometer sized pores with realistic pressures. In addition, both the polyethylene glycol and ammonium sulfate can be easily removed from the membrane with water and both are acceptable non-toxic reagents for many pharmaceutical applications. The biological acceptance of this liquid system contrasts with the methanol/isobutanol/water system of the prior art which is biologically toxic.

The following examples illustrate the invention and are not intended to limit the same.

EXAMPLE 1

The developed liquid-liquid intrusion integrity test was employed to correlate and predict the $\Phi$X-174 (a 28 nm bacteriophage) retention capabilities of Viresolve/70 TM and Viresolve/180 TM membranes, marketed by Millipore Corporation, Bedford, Mass., and various prototypical membranes made in accordance with Example 1 of U.S. Pat. No. 5,017,292 with Kynar concentrations ranging from 20 to 21% and casting temperatures ranging from 8° to 15° C. The specific two phase liquid system employed in this example consisted of the two phases formed upon the mixing of polyethylene glycol, molecular weight 8000 (PEG-8000), ammonium sulfate, and deionized water in the weight ratio 10:15:75, which was prepared and allowed to equilibrate for at least 6 hours. This two phase system was selected since both the major constituents, PEG 8000 and ammonium sulfate, are easily flushed from the Viresolve TM membrane pore structure and both are acceptable non-toxic reagents for pharmaceutical applications.

The instrument illustrated in FIG. 1 was configured to measure the liquid-liquid intrusion flow rate ratios for the various tested membrane samples. As shown in FIG. 1, an intrusion liquid, e.g., the ammonium sulfate rich bottom phase in the two phase system employed in this example, is housed within pressure dispensing vessel 10. Pressurized gas is supplied to pressure dispensing vessel 10 from a regulated and controlled pressure source (not shown) via conduit 12 and pressure dispensing vessel 14, an empty tank used for pressure dampening purposes. When valve 16 is opened, pressurized intrusion liquid passes through conduit 18 and T connection 20, at which point the intrusion phase pressurized is measured by pressure transducer 22 and is continually monitored and controlled. Intrusion liquid proceeds to pass through conduit 24, a flow rate measuring device 26 such as a Thermalpulse unit (M-Tek Corporation, Pittsburgh, Pa.) which continually monitors the intrusion phase flow rate, and conduit 28 to membrane test cell 30 which houses the desired membrane sample to be tested. The membrane sample 32, which is prewet with the PEG-8000 rich top phase by allowing the membrane sample 32 to sit in the wetting phase for 5 minutes, is positioned within test cell 30 so that pressurized intrusion liquid in conduit 28 passes through the membrane 32 and into receptacle 34 below the test cell 30. The membrane sample 32 is positioned in test cell 30 such that the skinned surface faces upstream, the normal orientation of the Viresolve TM membranes according to typical operating protocols. The regulated source pressure (not shown) is then increased until the desired system pressure is achieved as measured by pressure transducer 22.

The desired system pressure was determined in the following manner. For the PEG:ammonium sulfate:water system employed in this example, the interfacial surface tension between the two immiscible phases, as reported in the literature, lies between 0.2 and 2 dyne/cm. In addition, it is desired to have a correlation that predicts the retention of $\Phi$X-174, a 28 nanometer bacteriophage. Assuming cylindrical pores with circular apertures and a contact angle of 0, the Young/Laplace equation, given by equation 1, predicts an approximate pressure range of 4-40 psi is required to selectively intrude those pores greater than 28 nanometers, depending on the actual interfacial surface tension. It is then necessary to experimentally determine the optimum pressure within this range that gives the best correlation and maximizes the test sensitivity.

The regulated source pressure (not shown) is increased until the system pressure measured by pressure transducer 22 reads 4 psid, the lowest pressure within the desired range. The system is allowed to equilibrate for 10 minutes at which time the intrusion phase flow rate is measured by averaging the flow readings from the flow unit 26 over a 1 minute time span. The source pressure is increased to 5 psid, and again the system is allowed to equilibrate for 10 minutes before measuring the equilibrium intrusion phase flow rate. The system pressure is incrementally increased and the above procedure repeated until the entire pressure range of interest is spanned.

After the intrusion phase flow rate corresponding to the highest system pressure is measured, the entire system is purged of intrusion liquid by removing pressure dispensing vessel 10, discarding contents, and increasing the regulated source pressure to 20 psid. After the lines are completely purged, deionized water is placed into pressure dispensing vessel 10 for subsequent water permeability testing. The regulated source pressure is incrementally increased until the system pressure measured by pressure transducer 22 reads 5 psid, the desired transmembrane pressure drop for determining the membrane water permeability values. The system is allowed to equilibrate for 5 minutes at which time the water flow rate is measured by averaging the flow readings from the flow unit 26 over a 1 minute time span. Finally, the integrity test values for the membrane sample at each tested pressure are calculated as the logarithm of the corrected flow rate ratio given by $$\text{Integrity Test Value } (P) = \log\left(\frac{\frac{P}{5} Q_{water}}{Q_P}\right) \quad (3)$$

where P is the system pressure corresponding to the intrusion phase flow rate, $Q_P$, and $Q_{water}$ is the water flow rate measured at 5 psi. The P/5 ratio in the numerator of equation 3 is used to correct for pressure differences between the water flow rate and intrusion flow rate measurements.

To determine the virus retention capabilities of the tested membrane lots, samples from each membrane lot were challenged with a solution containing ΦX-174, a 28 nanometer bacteriophage, in phosphate buffered saline in a tangential flow cell under conditions of 1500 sec$^{-1}$ shear and a flux of 0.005 cm/min. Samples of the permeate and feed solutions were assayed for ΦX-174 concentration by a plaque assay using its host bacteria. A dilution series was generated to determine the absolute concentrations within both the permeate and feed streams. The membrane LRV was calculated as the logarithm of the ratio of the feed concentration to the permeate concentration.

Figure 2:
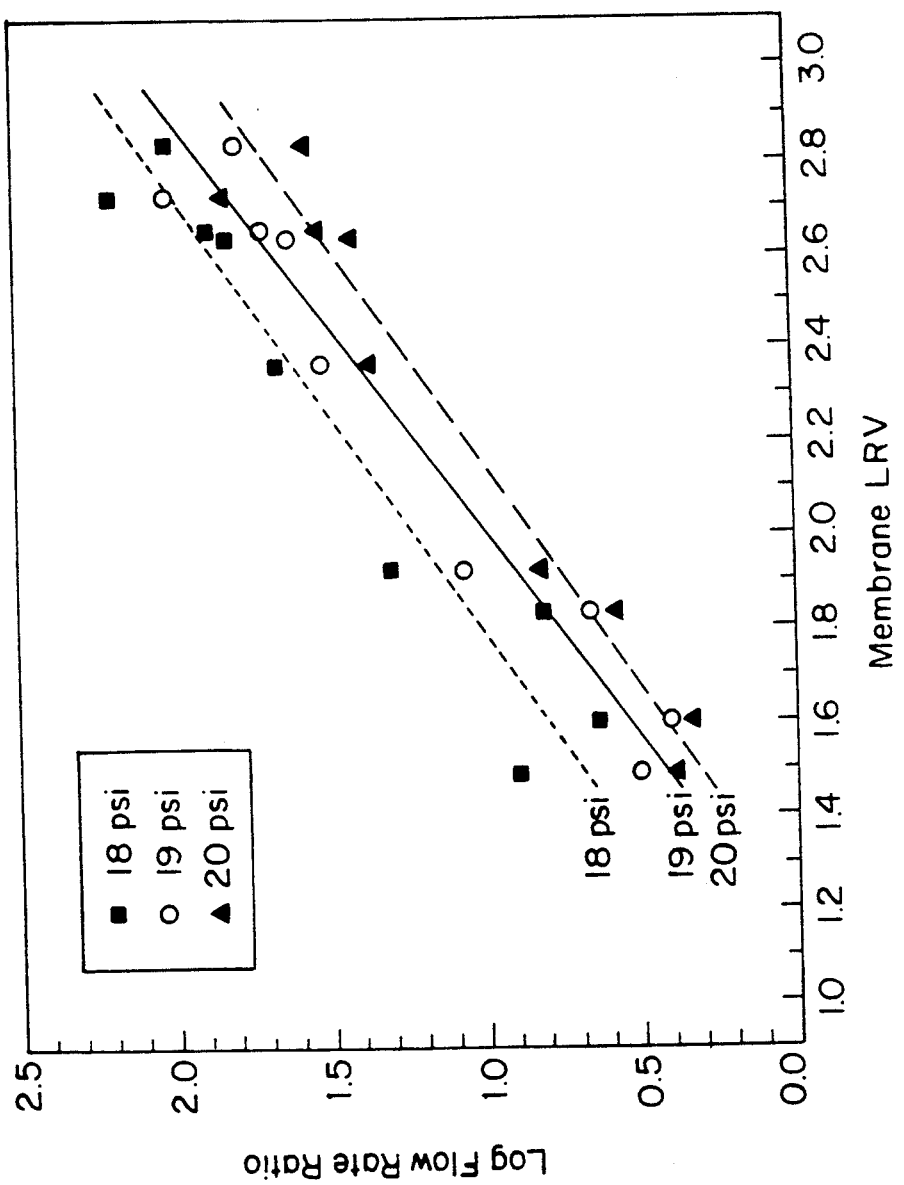
FIG. 2 are standard curves developed in accordance with Example 1 at test pressures of 18, 19, and 20 psi.

FIG. 2 shows the resulting integrity test log flow rate ratio as a function of membrane ΦX-174 LRV for the various tested membrane samples at transmembrane pressures of 18, 19, and 20 psi. As seen in FIG. 2, there is a strong linear correlation between the particle retention capabilities of the membrane samples and integrity test flow rate ratio at each of the shown pressures, with the best correlation obtained at 19 psi. At pressures below 18 psi, the sensitivity of the developed liquid intrusion test for detecting changes in membrane LRV decreases, resulting in a sub-optimal correlation. Similarly, at pressures greater than 20 psi, the sensitivity of the liquid intrusion test is again sacrificed. From this information, 19 psi was determined to be the optimal test pressure for correlating the passage of ΦX-174.

Figure 3:
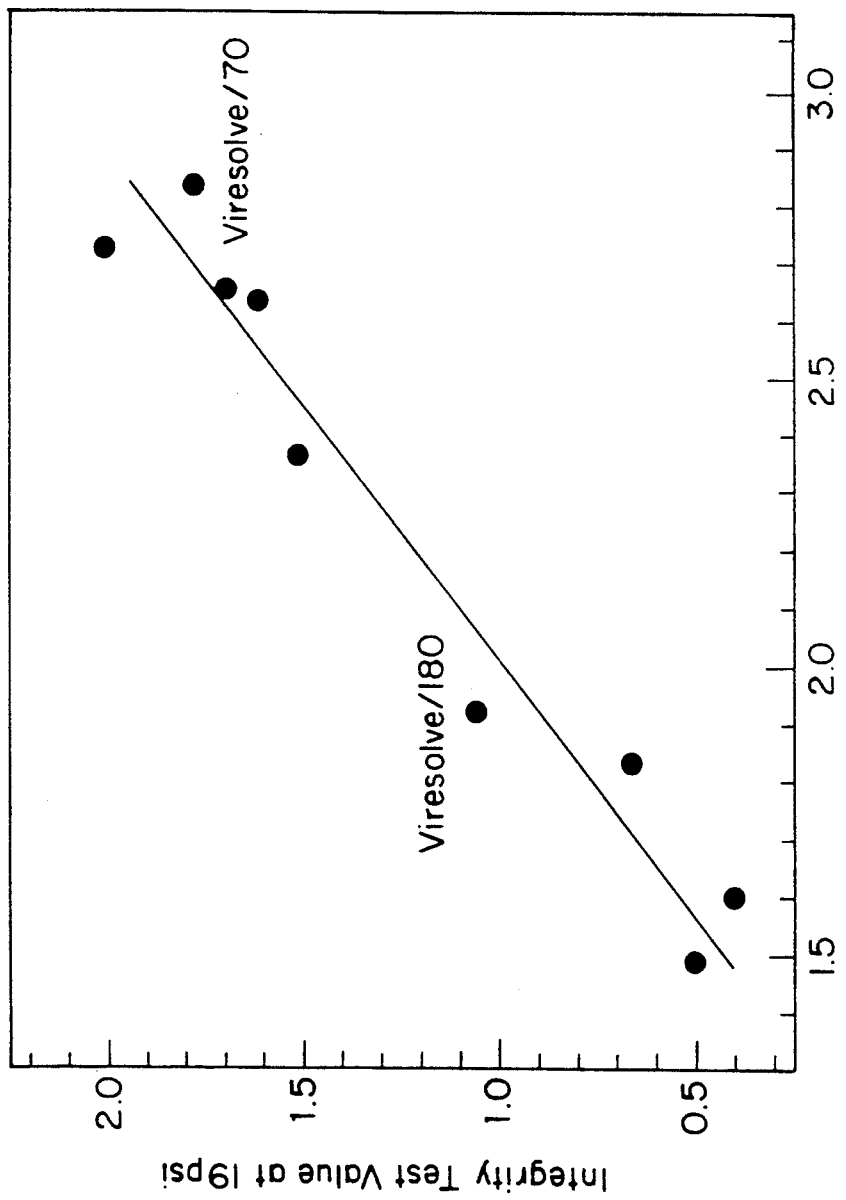
FIG. 3 is a standard curve developed in accordance with Example 1.

FIG. 3 shows the resulting integrity test value measured at 19 psi as a function of membrane ΦX-174 retention for the various tested membrane lots. As expected from theoretical arguments, there is a strong linear correlation between the particle retention capabilities of the membrane samples and integrity test flow rate ratios. In addition, a 3 LRV membrane is easily distinguishable from a 2.3 LRV membrane, which is easily distinguishable from a 1.5 LRV membrane. In other words, the difference between a membrane which removes 99.9% (3 LRV) of the bacteriophage and one which removes 99.5% (2.3 LRV) of the virus is easily discernible.

EXAMPLE 2

The developed liquid-liquid intrusion integrity test was also employed to correlate and predict the ΦX-174 (a 28 nm bacteriophage) retention capabilities of PZHK and Viresolve/70 ™ membranes, marketed by Millipore Corporation, Bedford, Mass., as well as various prototypical membranes made in accordance with Example 1 of U.S. Pat. No. 5,017,292 with Kynar concentrations ranging from 20 to 21% and casting temperatures ranging from 8° to 15° C. The specific two phase liquid system employed in this example again consisted of the two phases formed upon the mixing of polyethylene glycol, molecular weight 8000 (PEG-8000), ammonium sulfate, and 18 deionized water in the weight ratio 10:15:75.

The same instrument as used in Example 1 and illustrated in FIG. 1 was again configured to determine the liquid-liquid intrusion flow rate ratios with the actual intrusion flow through flow cell 26 now monitored by measuring the resulting pressure drop through a capillary coil. As before, the membrane sample 32, which is prewet with the PEG-8000 rich top phase in a synonymous fashion to Example 1, is positioned skinned surface upstream within test cell 30 so that pressurized intrusion liquid in conduit 28 passes through the membrane 32 and into receptacle 34 below the test cell. By means of an air regulator, the source pressure (not shown) is gradually increased until the system pressure as measured by pressure transducer 22 equilibrates to 19 psid, the desired transmembrane pressure which approximately corresponds to the selectively intrusion of those membrane pores greater than 28 nanometers in size and was empirically determined to be the optimal pressure for correlating the passage of ΦX-174 as illustrated in Example 1. During this pressure equilibration process, extreme care is taken to assure that the system pressure as measured by pressure transducer 22 does not exceed 19 psi, since higher pressures will result in the selective intrusion of smaller diameter pores. After the pressure equilibration process, the intrusion phase flow rate is calculated from the pressure drop across the capillary coil and a calibration curve relating this pressure drop to the actual intrusion phase flow rate.

After the intrusion phase flow rate at 19 psid transmembrane pressure is calculated, the source pressure (not shown) is gradually increased until the system pressure as measured by pressure transducer 22 equilibrates to 28 psid. This pressure was selected since it approximately corresponds to the complete intrusion of all the pores present in the membrane samples. Again, the intrusion phase flow rate at this elevated pressure condition is calculated from the pressure drop across the capillary coil and the calibration curve relating this pressure drop to the actual intrusion phase flow rate. From the calculated flow at this elevated transmembrane pressure, it is thus possible to obtain a measure of the total membrane permeability, a value synonymous to the water permeability value measured in Example 1. Finally, the integrity test value for each membrane sample tested is calculated as the logarithm of the ratio of 0.68 (19/28) times the intrusion phase flow rate measured at 28 psid to the intrusion phase flow rate measured at 19 psid. The 0.68 factor (19/28) is used to correct for the pressure differential between the 28 psid and 19 psid intrusion flow rate measurements.

Figure 4:
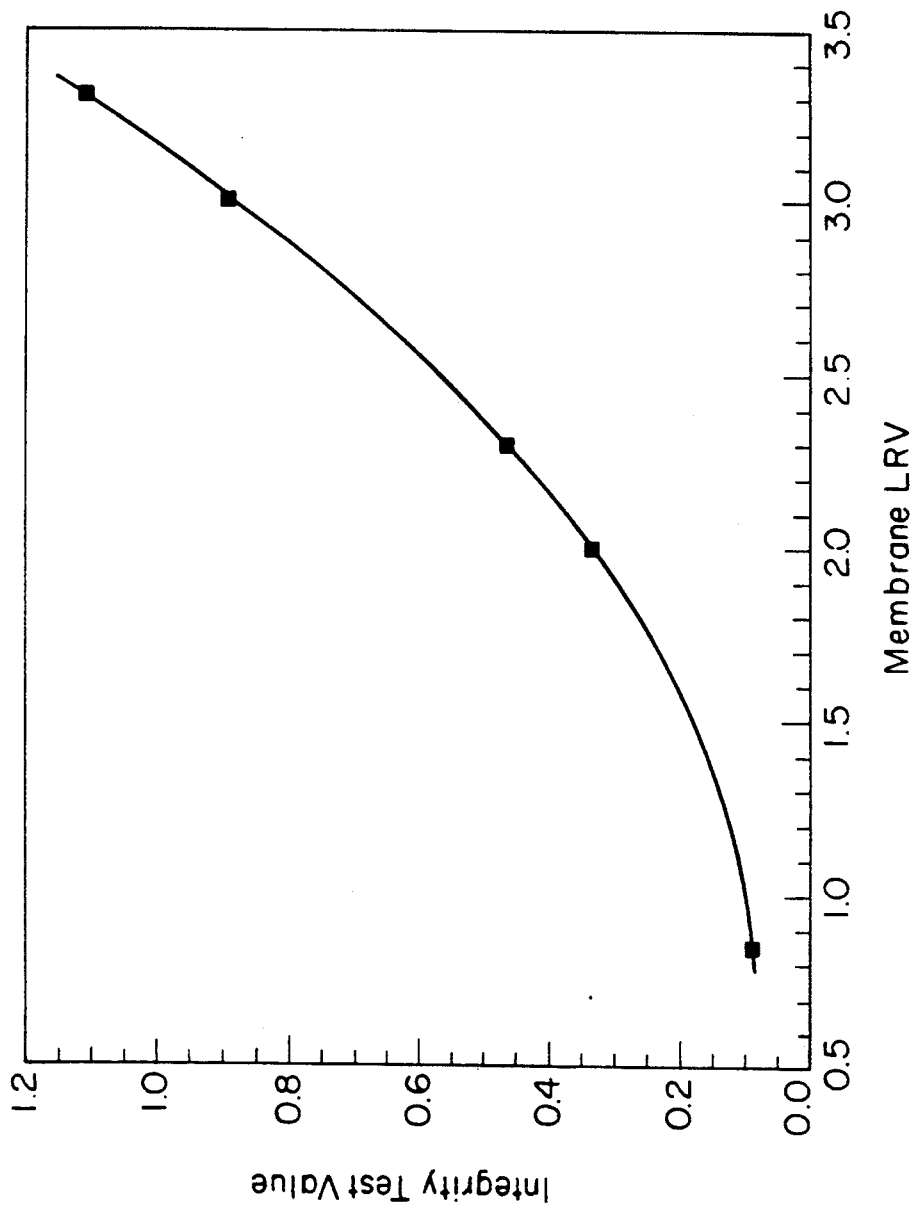
FIG. 4 is a standard curve developed in accordance with Example 2.

FIG. 4 shows the resulting integrity test log flow rate ratio as a function of membrane ΦX-174 LRV for the various tested membrane samples. The membrane ΦX-174 LRV values were determined using the same experimental protocol as discussed in Example 1. As seen in FIG. 2, there is a strong correlation between the particle retention capabilities of the membrane samples and integrity test flow rate ratios. As in Example 1, a 3 LRV membrane is easily distinguishable from a 2.3 LRV membrane, which is easily distinguishable from a 1 LRV membrane. Qualitatively, the results in FIG. 4 are very similar to those in FIG. 3, although the absolute values are somewhat different. This is to be expected since a different normalization factor was used in each example—water flow rate at 5 psi in Example 1 and intrusion phase flow rate at 28 psi in Example 2. Therefore, in developing the predictive particle retention correlation, any operating condition or membrane property which correlates to the total membrane permeability can be used as an appropriate normalization factor in the integrity test correlation as long as one is consistent.

We claim:

1. The process for non-destructively testing an ultrafiltration membrane to determine the particle retention capabilities of the membrane which comprises:

determining a standard relationship between the degree of retention of particles having a minimum size or larger by first set of membranes with a first factor consisting of the ratio of the flow-rate of a first intrusion liquid through said first set of membranes wet with a wetting liquid immiscible with said first intrusion liquid measured at a constant said first set of membranes measured at a constant transmembrane pressure that effects nearly complete intrusion of pores of said membrane, wetting a sample of said membrane with said wetting fluid, passing said first and second intrusion liquids at said pressures through said sample of said membrane to determine a second factor consisting of the ratio of flow rate of said first intrusion liquid through said membrane sample wet with said wetting liquid immiscible with said first intrusion liquid measured at said constant transmembrane pressure to the flowrate of said second intrusion liquid through said membrane sample measured at said constant transmembrane pressure that effects nearly complete intrusion of pores of said membrane sample, comparing said second factor ratio with said standard relationship thereby to determine the degree of retention of said particles having a minimum size or larger by said sample of said membrane, said wetting fluid and said intrusion fluid being nondestructive to said membrane, and said transmembrane pressures and said transmembrane flow rates being nondestructive to said membrane.

2. The process of claim 1 wherein said measured flow rates are established by directly setting said transmembrane pressures.

3. The process of claim 1 wherein said flow rates are adjusted so as to achieve said transmembrane pressures.

4. The process of any one of claims 1, 2 or 3 wherein the said first intrusion fluid and said second intrusion fluid are identical.

5. The process of any one of claims 1, 2 or 3 wherein the second intrusion liquid is water.

6. The process of any one of claims 1, 2, or 3 wherein said first intrusion liquid and said second intrusion liquid are water rich in ammonium sulfate and lean in polyethylene glycol and is essentially equilibrated with said wetting liquid comprised of water rich with polyethylene glycol and lean in ammonium sulfate and wherein said intrusion liquid is immiscible with said wetting liquid.

7. The process of any one of claims 1, 2, or 3 wherein said membrane is an ultrafiltration membrane.

8. The process of any one of claims 1, 2 or 3 wherein said membrane is a composite membrane which functions as an ultrafiltration membrane.

9. The process of claim 4 wherein said membrane is an ultrafiltration membrane.

10. The process of claim 4 wherein said membrane is a composite membrane which functions as an ultrafiltration membrane.

11. The process of claim 5 wherein said membrane is an ultrafiltration membrane.

12. The process of claim 6 wherein said membrane is an ultrafiltration membrane.

13. The process of claim 5 wherein said membrane is a composite membrane which functions as an ultrafiltration membrane.

14. The process of claim 6 wherein said membrane is a composite membrane which functions as an ultrafiltration membrane.

* * * * *

UNITED STATES PATENT AND TRADEMARK OFFICE
CERTIFICATE OF CORRECTION

PATENT NO.    : 5,282,380 Page 1 of 1
DATED         : February 1, 1994
INVENTOR(S)   : Anthony J. DiLeo et al.

It is certified that error appears in the above-identified patent and that said Letters Patent is hereby corrected as shown below:

<u>Column 11,</u>
Line 32, after "constant" add -- transmembrane pressure to the flow rate of a second intrusion liquid through --.

Signed and Sealed this

Fourth Day of November, 2003

JAMES E. ROGAN
*Director of the United States Patent and Trademark Office*